United States Patent
Djennati et al.

(10) Patent No.: US 9,046,512 B2
(45) Date of Patent: Jun. 2, 2015

(54) LOW VOLUME ASSAY APPARATUS

(75) Inventors: Nasser Djennati, Cheshire (GB); Andrew Mitchell, Lanchashire (GB)

(73) Assignee: BIO AMD HOLDINGS LIMITED, London (GB)

( * ) Notice: Subject to any disclaimer, the term of this patent is extended or adjusted under 35 U.S.C. 154(b) by 87 days.

(21) Appl. No.: 13/809,367

(22) PCT Filed: Jul. 11, 2011

(86) PCT No.: PCT/GB2011/051292
§ 371 (c)(1), (2), (4) Date: Mar. 29, 2013

(87) PCT Pub. No.: WO2012/004612
PCT Pub. Date: Jan. 12, 2012

(65) Prior Publication Data
US 2013/0195722 A1    Aug. 1, 2013

(30) Foreign Application Priority Data
Jul. 9, 2010   (GB) .................................. 1011581.4

(51) Int. Cl.
*G01N 21/75*   (2006.01)
*G01N 33/49*   (2006.01)
(Continued)

(52) U.S. Cl.
CPC ..... *G01N 33/4905* (2013.01); *B01L 2300/0864* (2013.01); *G01N 15/1434* (2013.01);
(Continued)

(58) Field of Classification Search
CPC .......... B01L 3/5027; B01L 2300/0816; B01L 2300/0825; B01L 9/527; B01L 2300/0864; B01L 3/502715; G01N 33/4905; G01N 11/14; G01N 1/31; G01N 15/1434

USPC ............... 422/52, 82.05, 82.06, 82.07, 82.08, 422/82.09, 82.11, 407, 500, 501, 50, 2, 503, 422/504, 930; 436/52, 53, 164, 165, 172, 436/174, 518, 524, 525, 526, 805, 809; 435/164, 165, 283.1, 287.1, 287.2, 435/288.7, 808, 4, 5, 7.2, 7.9
See application file for complete search history.

(56) References Cited

U.S. PATENT DOCUMENTS

2004/0224419 A1   11/2004   Zheng et al.
2008/0206880 A9*   8/2008   Clague et al. ................... 436/69

FOREIGN PATENT DOCUMENTS

EP    0180514 A2    5/1986
EP    2228657 A1    9/2010
(Continued)

*Primary Examiner* — Dennis M White
(74) *Attorney, Agent, or Firm* — Barlow, Josephs & Holmes, Ltd.

(57) ABSTRACT

Apparatus (1) for determining a property of a sample. The apparatus has a chamber (11, 13) for receiving at least a part of the sample and contains a rotor (15) adapted to rotate within the chamber (11, 13). The apparatus (1) also has a space (17) between the rotor (15) and the chamber (11, 13) which may be at least partially occupied by the sample, driving means (14) for rotating the rotor (15), and a detector (39) arranged to detect the rate of rotation of the rotor (15). The apparatus may also have two parts, a sample strip (5) for receiving the sample and a receiving member (3) for receiving the sample strip (5) and carrying out measurements on the sample. The rotor (15) may be magnetized across its diameter. The driving means (14) may be a magnetic driving means. The sample may be a blood sample. The property to be determined by the sample may be the prothrombin time of the blood or plasma.

21 Claims, 7 Drawing Sheets

(51) Int. Cl.
*G01N 11/14* (2006.01)
*G01N 15/14* (2006.01)
*G01N 1/31* (2006.01)
*B01L 9/00* (2006.01)
*B01L 3/00* (2006.01)

(52) U.S. Cl.
CPC .......... *G01N 1/31* (2013.01); *B01L 2300/0816* (2013.01); *B01L 9/527* (2013.01); *B01L 3/5027* (2013.01); *B01L 3/502715* (2013.01); *B01L 2200/027* (2013.01); *B01L 2300/0654* (2013.01); *B01L 2300/0825* (2013.01); *B01L 2300/1805* (2013.01); *B01L 2400/0406* (2013.01); *B01L 2400/0409* (2013.01); *B01L 2400/043* (2013.01); *G01N 11/14* (2013.01); *G01N 2011/147* (2013.01)

(56) References Cited

FOREIGN PATENT DOCUMENTS

| WO | 03083489 | A1 | 10/2003 |
| WO | 2005047895 | A1 | 5/2005 |
| WO | 2005106466 | A1 | 11/2005 |
| WO | 2006100443 | A2 | 9/2006 |
| WO | 2009069656 | A1 | 6/2009 |

* cited by examiner

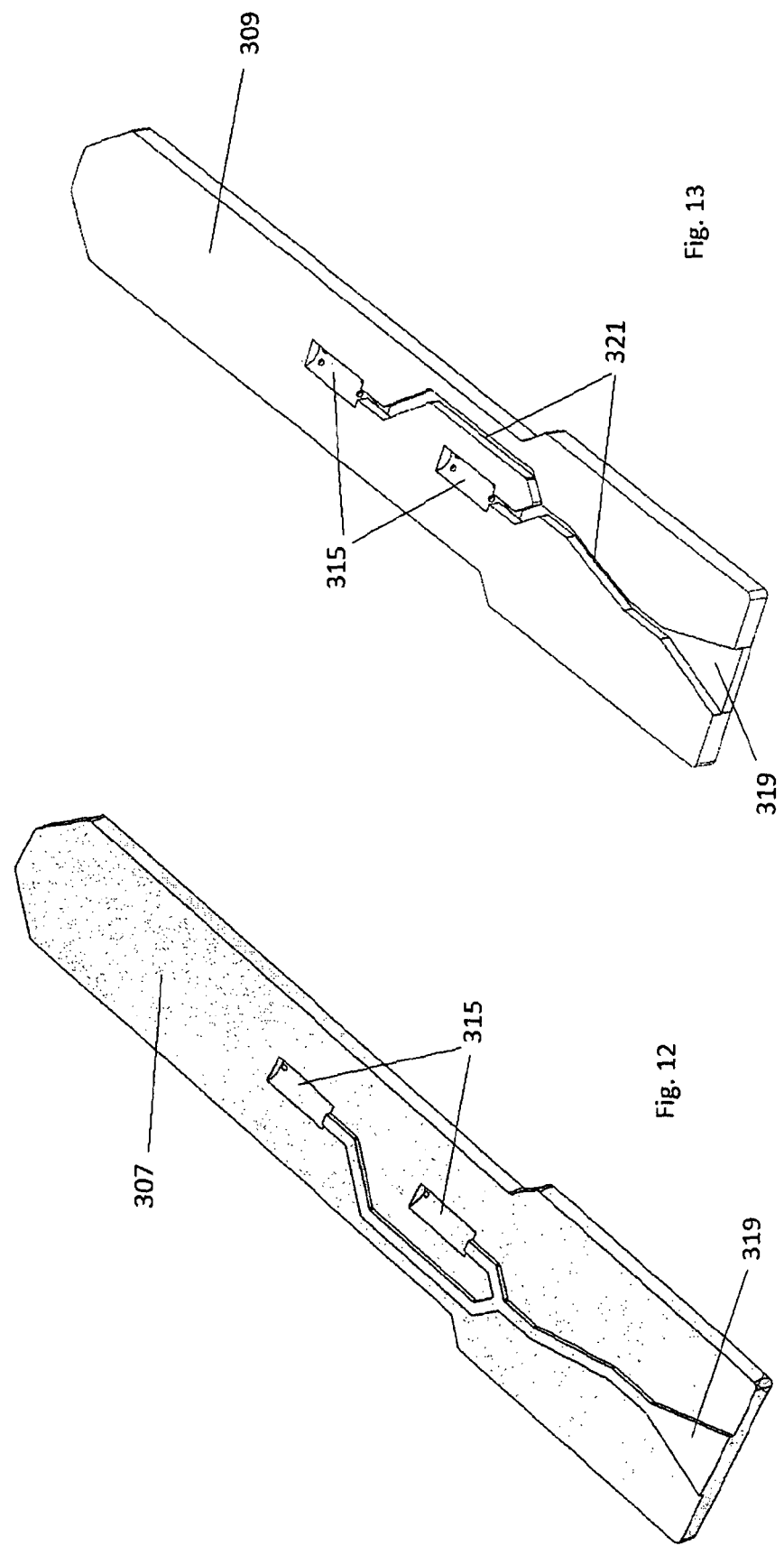

LOW VOLUME ASSAY APPARATUS

The present invention relates to low volume assay apparatus for determining a physical property of a sample such as blood.

The present invention is, in particular but not exclusively, concerned with measuring the coagulation of blood which includes clotting or clot formation assays such as measurement of coagulation time or prothrombin time (PT) of blood or plasma; clotting parameter assays such as rate or amount of clot formation and/or dissolution, degree of platelet aggregation, activated partial thromboplastin time (APTT), activated clotting time (ACT), time required to form a fibrin clot, protein C activation time (PCAT), thrombin time (TT) and Russell's viper venom time (RVVT); and non-clotting properties of a fluid such as the measurement of blood or plasma viscosity and blood haematocrit.

The ability to determine a property of a sample such as blood is desirable because it enables various treatments to be tailored to a particular patient's condition. For example, blood coagulation (its ability to clot) is characterised by a series of biochemical reactions in which fibrinogen forms cross-linked polymeric film. The ability to determine parameters associated with the coagulation process facilitates the monitoring of anticoagulant drug doses. Such drugs are typically prescribed to patients who are at risk from thrombolic abnormalities. One commonly used coagulation parameter is the coagulation time or prothrombin time (PT) of blood or plasma. PT is typically expressed as an internationalised normalised ratio (INR) (the ratio between the coagulation time of a sample of blood and the normal coagulation time). The INR for a patient with normal blood is 1 but for a patient with clotting problems the INR can be as high as 7 or 8.

A known system for determining the PT of blood or plasma is a laboratory based system that requires wet mixing of a suitable coagulation accelerator reagent (e.g. thromboplastin) with the sample of interest. Such a system is expensive to manufacture, bulky and, thus, not very portable, and must also be operated by a skilled technician. It also requires the presentation of a large sample volume of venous blood which is undesirable for the patient. Such systems are typically found in laboratory facilities associated with cardiovascular care units and in dedicated specialist phlebotomy clinics.

A known assay system that may be used by clinicians or patients without the requirement for specific expertise is disclosed in WO2007101993. This describes an apparatus that may be used to determine a coagulation parameter of a blood sample. The apparatus includes a sample strip-receiving member configured to receive a sample strip that has a chamber. The chamber includes a magnetically susceptible particle whose response to an oscillating magnetic field may be detected to determine clot formation times, clot dissolution times or clotting parameters.

Another known assay system is disclosed in U.S. Pat. No. 5,110,727 which describes a method and apparatus for the measurement of clot formation times, clot dissolution times, or clotting parameters. This method performs these measurements by monitoring movement of magnetic particles incorporated in the sample being assayed, where the movement is induced by a magnetic field.

Use of this type of system for self-diagnosis by the patient is limited due to the high associated cost. To achieve 'gold standard' accuracy levels without the need for an expert operator, a highly complex and costly manufacturing process is required. A further problem with such systems is that they involve observing the movement of magnetically susceptible particles suspended within the sample as it coagulates and its viscosity changes. Since the particle moves within the sample, the particle itself can interfere mechanically with the fibrin clot and therefore lead to difficulties in obtaining an accurate measurement of PT.

With existing anticoagulant drug regimens such as heparin and warfarin and the introduction of new generation anticoagulant drugs there is increasing demand for patient or near patient monitoring of PT (INR) to enable anticoagulant drug regimens to be safely administered and controlled. The above described known systems fail to satisfactorily achieve this.

An object of embodiments of the present invention is to provide an apparatus that may be operated by an unskilled user and which is capable of producing accurate and repeatable PT measurements and/or associated blood coagulation parameters from very low capillary blood sample volumes that might be less than 3 µl (comparable to sample size for monitoring of blood sugar levels of diabetic patients). In addition, it is an object to produce an apparatus that is relatively cheap to manufacture and which does not require tight manufacturing tolerances.

According to an aspect of the present invention, there is provided apparatus for determining a property of a sample comprising a chamber for receiving at least a part of the sample, a rotor that is contained within the chamber and adapted to rotate about an axis, a space between the rotor and the chamber which may be at least partially occupied by the sample, a conduit that leads to the chamber and enables the chamber to be filled with the sample, a driving means adapted to drive the rotor, and a detector arranged to measure the rate of rotation of the rotor within the chamber.

Advantageously, since the rotor does not pass through the sample, it does not interfere with the physical property of the sample being measured such as coagulation time. Further, the rotor can be configured to rotate continuously within the chamber so that a continuous signal output from the rotating magnetic field is achieved which enables any change in frequency caused by the effect of the sample on the rotor to be easily detected. In addition, the apparatus can be configured so that the rotor rotates with very low frequencies to reduce its kinetic effect on the physical properties of the sample. Thus, a more accurate measurement of a property of the sample can be obtained than with conventional devices. In addition, the space that may be occupied by the sample and its proximity to the rotor allows better grip between the sample and the rotor and therefore more immediate feedback as to the status of the sample in the chamber which further enhances the accuracy of any measurements by the apparatus.

The apparatus may comprise a sample strip and a receiving member for receiving the sample strip and the sample strip may comprise the chamber. The sample strip may comprise two parts that may be joined together to form the chamber. The receiving member may comprise the driving means.

There may be two chambers and respective rotors within each chamber. There may be a magnetic driving means associated with each chamber. The two chambers may be substantially adjacent one another, in line with one another or offset relative to one another.

The driving means may be a magnetic driving means.

The or each rotor may comprise a permanent magnet and the magnetic driving means may be arranged to drive the corresponding rotor directly.

The detector may be arranged to detect changes brought about by the rotating magnetic field of the rotor.

There may be one or more secondary rotors which are coupled to the rotors in the chambers and the secondary rotors may be driven by the or each corresponding driving means thereby indirectly driving the rotors in the respective chambers. The secondary rotors may be permanent magnets and the detector may detect changes brought about by the rotating magnetic field of the secondary rotors to determine the rate of rotation of the rotors in the respective chambers. The sample strip or the receiving member may comprise the secondary rotors.

There may be a heater for heating the sample. There may be a temperature sensor to monitor the temperature of the sample and enable the operation of the heater to be adjusted accordingly depending upon the desired temperature of the sample.

There may be one or more optical detectors for monitoring the presence of the sample in the chamber. There may be a collection means which is connected to the or each chamber via the conduit, said collection means enabling the sample to be received into the or each chamber. The conduit may comprise one or more microfluidic channels. There may be an air vent connected to the or each chamber by one or more conduits.

The receiving member and the sample strip may have cooperating features that enable the two elements to engage one another. There may be a known quantity of reagent in the or each chamber to control the physical properties of the sample.

The apparatus may be adapted to determine one or more properties of a blood sample.

The or each rotor may comprise a permanent magnet and the detector may be arranged to detect changes brought about by the rotating magnetic field. The or each rotor may be magnetised across its diameter.

The chambers and the rotors may be substantially cylindrical in shape.

The electromagnetic field generator may also comprise the detector.

The sample may be a liquid. The sample may be blood or plasma.

The detector may be a Hall Effect sensor, a magneto-resistive device or a search coil.

According to a second aspect of the present invention, there may be provided a sample strip comprising at least one chamber which contains a rotor that can rotate within the chamber, the rotor being adapted to be driven by a magnetic driving means, and a conduit leading to the chamber to enable the chamber to be at least partially filled with a sample.

According to a third aspect of the present invention, there is provided a receiving member for receiving a sample strip according to the second embodiment comprising a slot for receiving the sample strip, a magnetic driving means adapted to drive the rotor and a detector arranged to detect the rate of rotation of the rotor within the chamber.

In order that the invention may be more clearly understood embodiments thereof will now be described by way of example with reference to the accompanying drawings of which:

FIG. 12 is a perspective view of a male section of a third embodiment of a sample strip; and FIG. 13 is a perspective view of the corresponding female section of a sample strip intended to engage the male section shown in FIG. 12 to form a complete sample strip.

Figure 1:
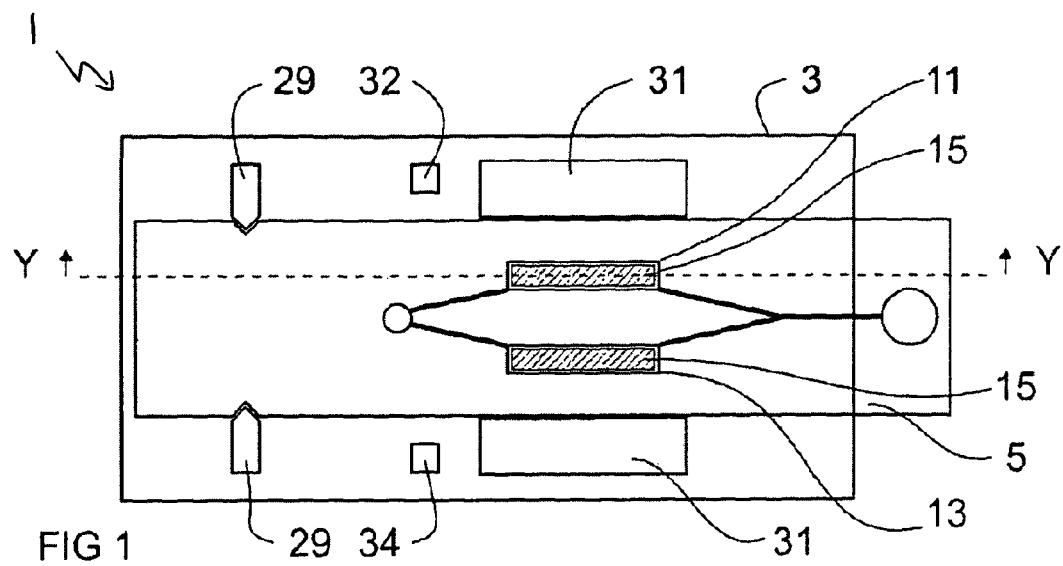
FIG. 1 is a plan view of a first embodiment of assay apparatus according to the present invention.
Figure 2:
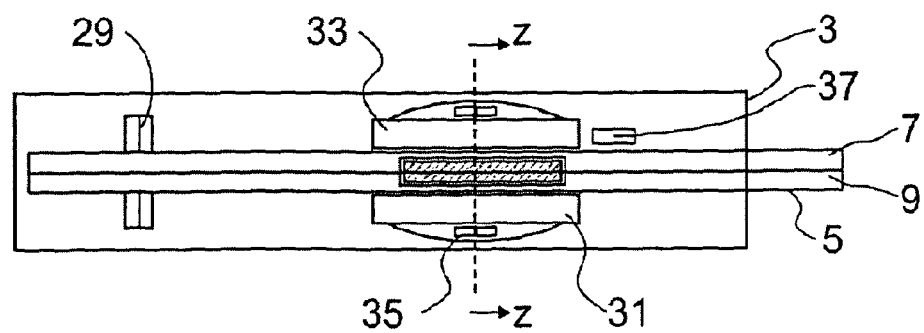
FIG. 2 is a cross section view of the assay apparatus shown in FIG. 1 taken along the line Y-Y.
Figure 3:
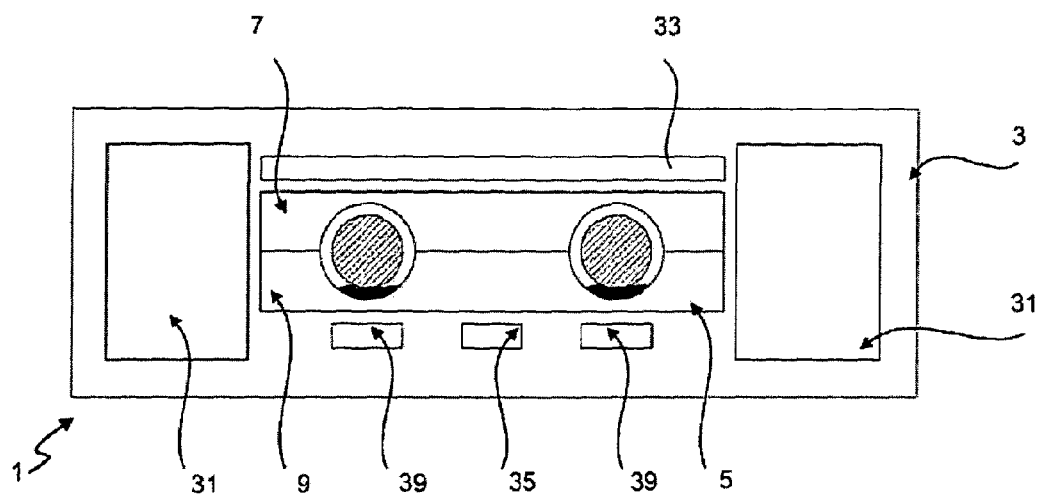
FIG. 3 is a cross section view of the assay apparatus shown in FIG. 2 taken along the line Z-Z.
Figure 4:
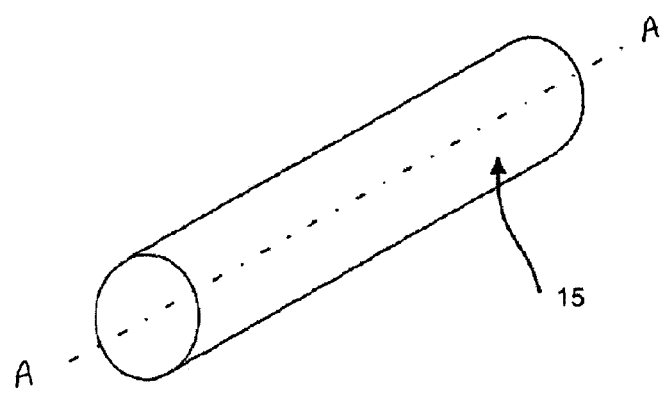
FIG. 4 is a perspective view of a rotor used in the assay apparatus shown in FIG. 1.
Figure 5:
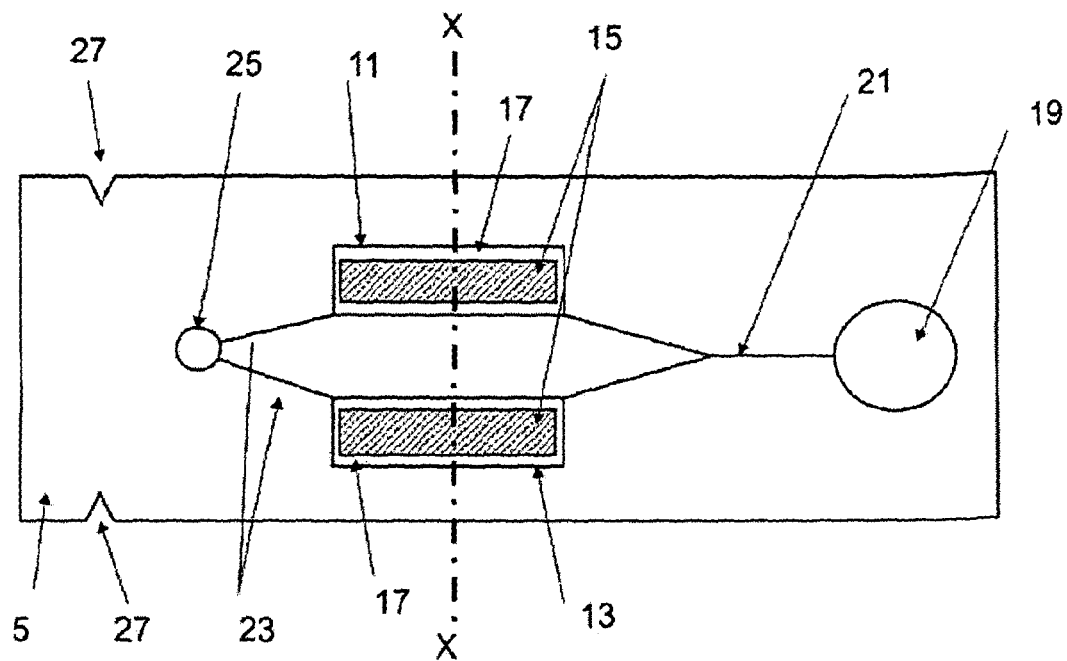
FIG. 5 is a plan view of a sample strip used in a first embodiment of assay apparatus according to the present invention.
Figure 6:
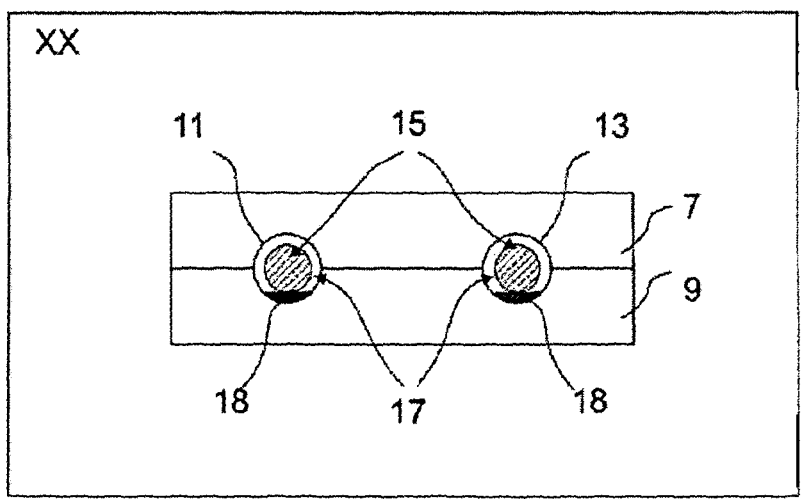
FIG. 6 is a cross section view of the sample strip shown in FIG. 5 taken along the line X-X.

The assay apparatus of the present invention is operable to measure the prothrombin time of a blood sample. It is of course obvious to the skilled man that the assay of the present invention could be suitably adapted to test other physical properties of a blood sample or other substances of interest or other types of sample.

Referring to the drawings there is shown an assay apparatus 1 comprising a sample strip reader 3 for receiving a sample strip 5. Both the sample strip reader 3 and the sample strip 5 are made from plastics material.

The sample strip 5 comprises separate upper and lower sections 7, 9 which each have two semi-cylindrical formations etched into their interfacing sides. Each semi-cylindrical formation is of substantially the same dimensions and is positioned such that, when the two sections 7, 9 are joined together, they form two separate cylindrical chambers 11, 13 that are substantially parallel and adjacent one another. Contained within each chamber 11, 13 is a substantially cylindrical rotor 15 comprising a ferromagnetic material such as iron. Optionally, the ferromagnetic material is encased in another material such as plastic to minimise the effect of the iron on the blood sample. Each rotor 15 is magnetised such that its poles are on opposite sides respectively of the rotor 15 across its diameter. This is to enable rotation of the rotors 15 when subjected to an alternating magnetic field.

The shape and dimensions of each rotor 15 is chosen such that it can freely rotate within its chamber 11, 13 but such that its lateral movement along the length of the chamber 11, 13 is limited. The shape and dimensions of each rotor are also chosen so that a space is formed between the rotor 15 and its chamber 11, 13 which can be occupied by the sample. In this embodiment, a chamber 11, 13 is approximately 3.2 mm in length and 1.2 mm in diameter and a rotor 15 is approximately 3.0 mm in length and 1.0 mm in diameter thereby giving 0.1 mm clearance around the rotor 15 within a corresponding chamber 11, 13. The volume of the space 17 and, thus, the volume of the sample necessary to fill the space 17 is therefore in the order of 1.3 µl or less. Other, smaller, dimensions and volumes are envisaged. A quantity of dried clotting reagent 18 is placed within the space 17 and is intended to mix with the blood sample. The amount of reagent 18 used in each chamber 11, 13 provides a degree of control over the clotting time of the blood sample when it enters the two chambers 11, 13.

The sample strip 5 further comprises a sample collection well 19 which is connected to the two chambers 11, 13 via a small microfluidic channel 21 which splits into two tributaries. Like the chambers 11, 13, the channel 21 is formed by corresponding formations etched into the interfacing sides of the two sections 7, 9. A second set of microfluidic channels 23, also etched into the interfacing sides of the two sections 7, 9, connects the chambers 11, 13 to an air vent 25 which extends to the outside of the upper section 7 of the sample strip 5. In this embodiment, the approximate dimensions of the channels are 0.25 mm×0.125 mm in cross section and 21 mm in length, thereby giving a blood volume for the channels of 0.66 μl. Thus, the combined volume of the channels and the chambers is approximately 3.25 μl. The air vent 25 and connecting channels 23 facilitate the progression of the sample from the collection well 19 to the chambers 11, 13 by encouraging capillary action. Toward the end of the sample strip 5 remote from the collection well 19, two recesses 27 are formed on opposite sides respectively of the sample strip 5. The recesses 27 act as seats for corresponding projections formed in the sample reader 3 and therefore facilitates the positioning and retention of the sample strip 5 when it is inserted into the reader 3.

The sample strip reader 3 comprises a slot into which the sample strip 5 may be inserted for measurements to be taken. The slot is shaped and configured to receive the sample strip in a relatively tight fit. Two spring mounted projections or clips 29 are provided inside the reader 3 and are positioned such that, when the sample strip 5 is inserted into the reader 3, the clips 29 are adjacent to and seated within the recesses 27 formed in the sample strip 5 to retain the sample strip 5 in place. If it is desired to remove the sample strip 5, gentle pressure of the sample strip 5 out from the reader 3 causes the clips 29 to disengage the sample strip 5 and permit it to be released. The angled relationship of the recesses 27 and the clips 29 facilitates the disengaging procedure.

Figure 7:
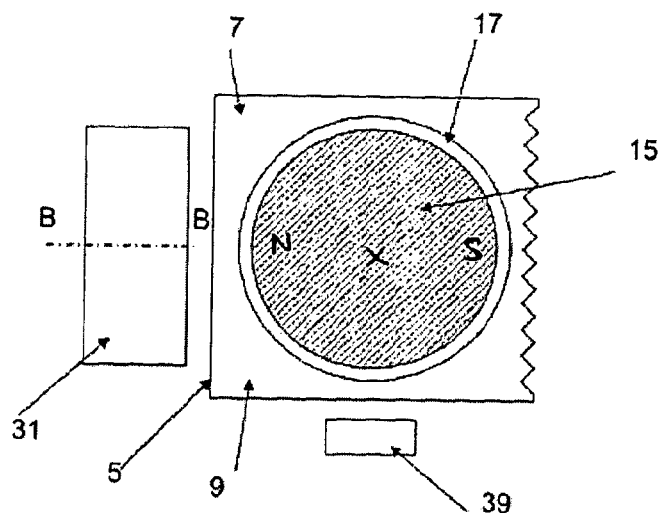
FIG. 7 is an enlarged cross section view of elements of the assay apparatus shown in FIG. 1.

The sample strip reader 3 also comprises electrical coils (solenoids) or electromagnetic field generators 31 which are positioned such that, when the sample strip 5 is inserted into the reader 3, the chambers 11, 13 are adjacent and in close proximity to the coils 31. The coils 31 are arranged to extend substantially perpendicularly away from its corresponding chamber 11, 13 such that one end lies adjacent its chamber 11, 13. Thus, when a current is passed through the coils 31, a magnetic pole is created adjacent the chamber 11, 13. The coils 31 are powered by a small battery unit 32 contained within the reader 3 and are configured to generate an alternating magnetic field along the axis denoted by B-B shown in FIG. 7. The alternating magnetic field is generated by passing an alternating current through the coils 31 and the frequency of the alternating current provides control over the coils affect on the rotors 15.

A heating element 33 is provided toward the upper surface of the reader 3 and is positioned to be substantially parallel with the upper section of the sample strip 5 and adjacent the two chambers 11, 13. The heating element 33 is also powered by the battery unit and serves to maintain the temperature of the sample at 37° C. (human body temperature) so as to replicate the conditions in the body. To maintain the sample at the desired temperature, a temperature sensor 35 is provided toward the lower portion of the reader 3 adjacent the lower section 9 of the sample strip 5 so that the temperature of the sample in the chambers 11, 13 can be monitored and the operation of the heating element 33 adjusted accordingly. The operation of the heating element 33 and the coils 31 is controlled by an electronic control means 34.

To determine the time at which the sample enters the chambers 11, 13, an optical detector 37 is provided which monitors the light levels within the chambers 11, 13. When the sample enters the chambers 11, 13 and fills the respective spaces 17, the light level drops to a predetermined level which signifies the starting time for the test (T zero). Measurement of the prothrombin time (PT) of the sample is facilitated by two magnetic field detectors e.g. Hall Effect sensors 39 which are positioned within the reader 3 such that they are substantially parallel with and adjacent to respective chambers 11, 13 when the sample strip 5 is inserted into the reader 3.

In use, a sample of blood from a patient is placed on the collection well 19 of the sample strip 5 and the sample strip 5 is inserted into the reader 3 until the clips 29 of the reader 3 engage the recesses 27 of the strip 5 to hold it in place. When the sample strip 5 is in place, the coils 31 of the reader are activated and an alternating magnetic field is generated across the two rotors 15. The alternating magnetic field causes the rotors 15 within the chambers 11, 13 to rotate due to the proximity of the differing poles of the rotors 15 to the corresponding poles of the field generated by the coils 31. When the pole of a rotor 15 and the pole of an adjacent coil 31 are alike at their closest proximity, the two poles repel one another and cause the rotor 15 to rotate. As the rotor 15 rotates within its chamber 11, 13, the opposite pole of the rotor 15 moves closer to and is attracted by the opposite pole of the coil 31. At the point at which the two opposite poles are at their closest proximity, the magnet field generated by the coil 31 is reversed and the aforementioned process repeats itself to maintain the rotating action of the rotor 15 within its chamber 11, 13. Through capillary action, assisted by rotation of the rotors 15, the sample proceeds from the collection well to the chambers 11, 13 via the channel 21 and gradually fills the two chambers 11, 13. Rotation of the rotors 15 helps to dissolve and mix the reagent 18 with the sample.

The rotating magnetic field of the rotor 15 gives rise to peak outputs detected by the adjacent Hall Effect sensor 39. The peak output corresponds to the point at which a pole of the rotor 15 passes in closest proximity to the sensor 39. By measuring the time between the peak outputs of the sensor 39 it is possible to determine the rotational velocity of the rotors 15.

When the chambers 11, 13 contain a predetermined quantity of the sample, which is indicated by a specific drop in light intensity as measured by the optical detector 37, the test start time is triggered. As the blood sample within the chambers 11, 13 coagulates and the viscosity of the sample changes, the resistance of the sample to the rotation of the rotors 15 increases, thereby reducing the rotational velocity of the rotors 15 as detected by the respective sensors 39. When a predetermined rotational velocity is measured which corresponds to coagulation of the sample, the timer is stopped and the PT is obtained. Alternatively, the PT can be obtained by measuring the increase in the current through the coils necessary to generate an electromagnetic field sufficient to maintain the rotational velocity of the rotors 15. When a predetermined current is reached, the sample can be considered to have completed its coagulation process. The two chambers 11, 13 operate independently and so can be used to obtain different PT measurements.

One of the chambers 11 contains enough dried reagent that any sample of blood that enters the chamber will coagulate in a given time regardless of its physical properties. This is the control chamber and indicates that a test has run properly. The other chamber 13 contains a known quantity of reagent that is sufficient to make the sample coagulate but not at the same time regardless of its physical properties. Thus, a normal sample of blood will coagulate quicker than an abnormal sample in this test chamber 13. Using the PT measurement from the test chamber 13 it is possible to extrapolate the INR value of the sample.

Figure 8:
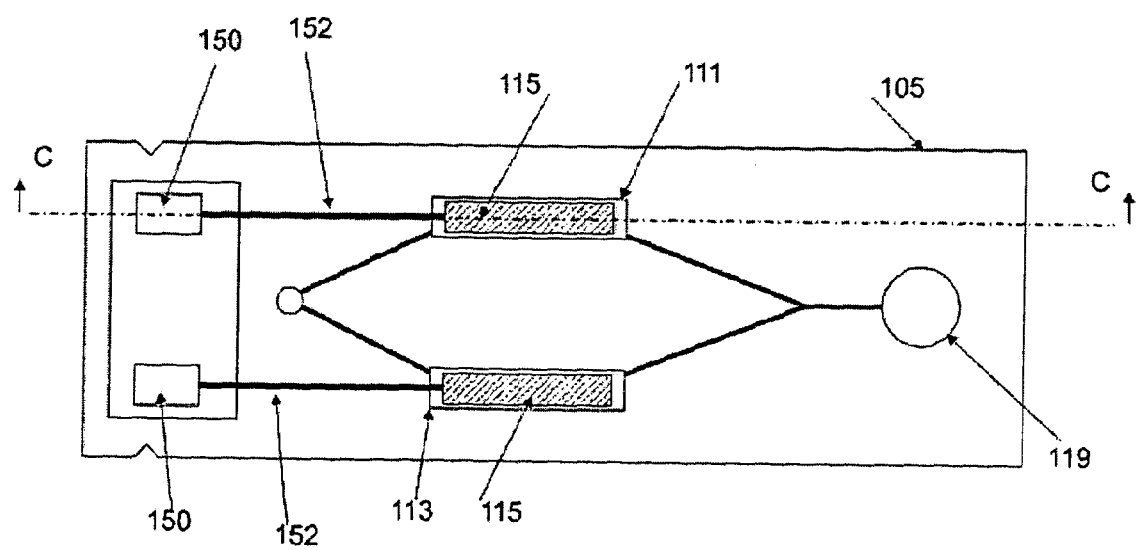
FIG. 8 is a plan view of an alternative sample strip.
Figure 9:
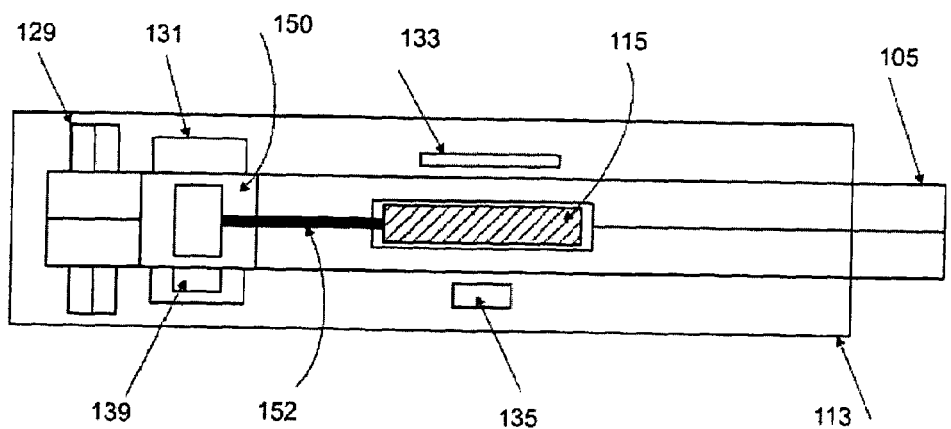
FIG. 9 is a cross section view of an alternative embodiment of assay apparatus according to the present invention comprising the sample strip shown in FIG. 8 along the line C-C.

Referring to FIGS. 8 to 9, in a second embodiment, the sample strip 105 comprises similar cylindrical chambers 111, 113 to those of the sample strip 5 of the first embodiment 1 and contains two substantially cylindrical rotors 115 that may freely rotate in the chambers 111, 113 about their longitudinal axes. The sample strip differs from that of the first embodiment in that the rotors 115 are connected to respective substantially cylindrical secondary rotors 150 by two drive shafts 152. In this embodiment, the secondary rotors 150 comprise ferromagnetic material with north and south poles across their respective diameters and they are driven to rotate by an external alternating magnetic field which is generated by adjacent coils 131. Since the secondary rotors 150 are coupled to the primary rotors 115 in the chambers 111, 113 by the drive shafts 152, rotation of the secondary rotors 150 as a result of the external magnetic field causes the primary rotors 115 to rotate at the same rate. Since the primary rotor 115 is driven by the secondary rotor 150, the primary rotor 115 can be made from a non-metallic material that is less likely to interfere with the dried reagent and the sample.

The velocity of rotation of the primary rotors 115 is determined by measuring the peak output of the magnetic field of the secondary rotors 150 when a pole passes an adjacent detector 139. The PT can therefore be obtained in the same way as that of the first embodiment as described above. In all other respects, the apparatus 101 of the second embodiment is substantially the same as the first embodiment.

Figure 10:
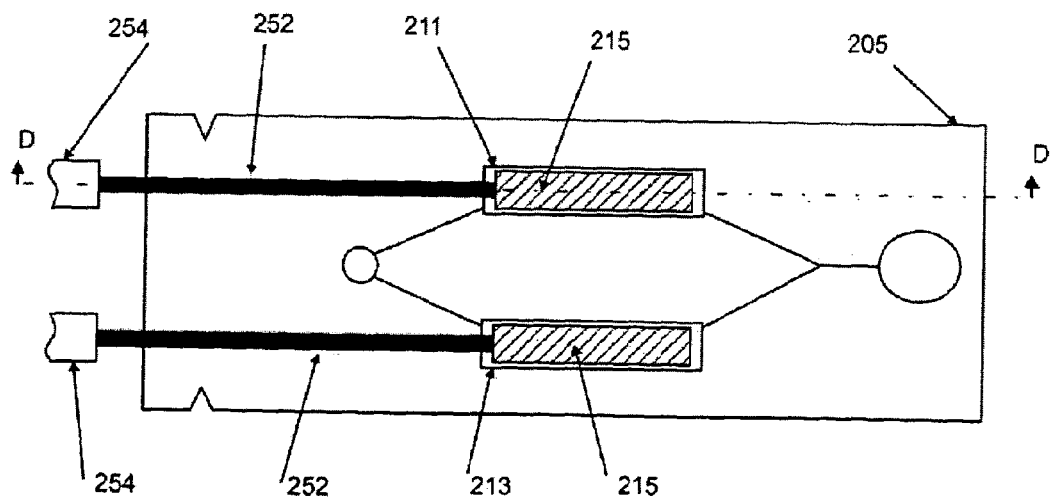
FIG. 10 is a plan view of an alternative sample strip.
Figure 11:
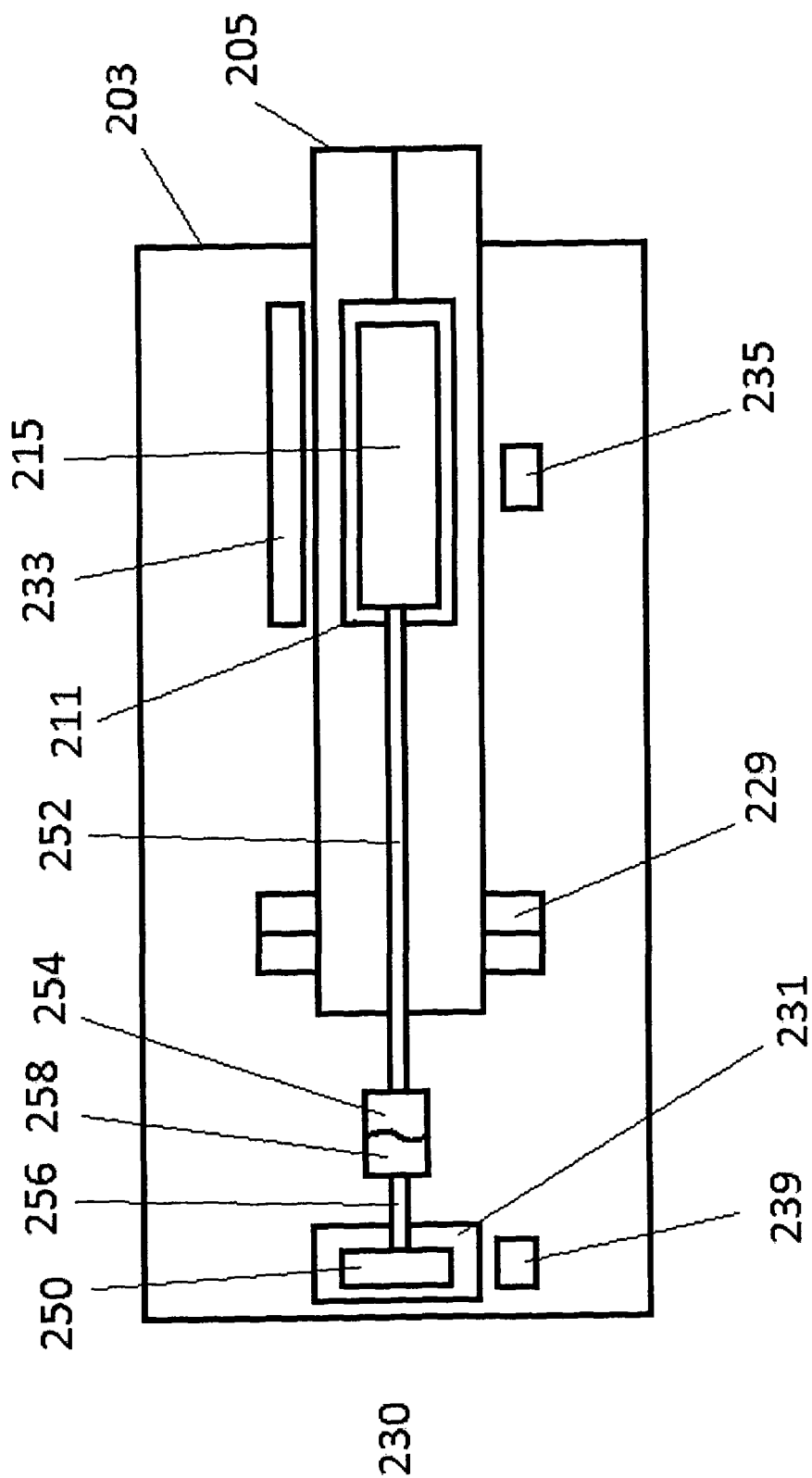
FIG. 11 is a cross section view of an alternative embodiment of assay apparatus according to the present invention comprising the sample strip shown in FIG. 10 along the line D-D.

Referring to FIGS. 10 to 11, in a third embodiment, the sample strip 205 comprises similar cylindrical chambers 211, 213 to those of the sample strips 5, 105 of the first and second embodiments 1, 101 and contains two substantially cylindrical rotors 215 that may freely rotate in the chambers 211, 213 about their longitudinal axes. In this embodiment, the primary rotors 215 within the chambers 211, 213 are driven by a driving mechanism 230 within the reader 203 which comprises two secondary rotors 250. The secondary rotors 250 comprise ferromagnetic material with north and south poles across their respective diameters. The secondary rotors 250 are driven by an external alternating magnetic field which is generated by adjacent coils 231. The rotational velocity of the secondary rotors 250 is measured by detecting the peak output from adjacent Hall Effect sensors 239 when the poles of the secondary rotors 250 pass in closest proximity to an adjacent sensor. Since the primary rotor 205 is driven by the secondary rotor 250, the primary rotor 215 can be made from a non-metallic material that is less likely to interfere with the dried reagent and the sample.

The primary rotors 215 each have a drive shaft 252 which extends out from an end of the sample strip body and terminates in a drive shaft coupling 254. Likewise, the secondary rotors 250 each have a drive shaft 256 that extends toward the space occupied by the strip reader 5 and which terminates with a drive shaft coupling 258. The respective drive shafts 252, 256 and drive shaft couplings 254, 258 are configured such that, when the sample strip 205 is inserted into the reader 203, the respective drive shaft couplings 254, 258 meet and engage one another, thereby coupling the secondary rotors 250 to the primary rotors 215. Rotation of the secondary rotors 250 under the influence of the external alternating magnetic field generated by the adjacent coils 231 therefore causes the primary rotors 215 to rotate at the same rate. The effect of the coagulation of the sample on the rotation of the primary rotors 215 has a corresponding effect on the rotation of the secondary rotors 250 and therefore enables the above described PT measurements to be taken via the sensors 239. In all other respects, the apparatus 201 of the third embodiment is substantially the same as the first embodiment but with the position of the various elements adjusted accordingly.

In a fourth embodiment, the sample strip 305 comprises two chambers 315 arranged such that they are substantially parallel with one another and along a common line as opposed to adjacent to one another. The position and path of the microfluidic channels 321 from the collection well 319 to the two chambers 315 is adjusted accordingly. In all other respects, the apparatus 301 is substantially the same as that of the first embodiment but with the cooperating elements positioned accordingly. The reader 303 and sample strip 305 could, though, be adapted to operate in the same way as the second or third embodiments but with the chamber positions in line as opposed to adjacent one another. The advantage of aligning the chambers along a common line is that it is easier to rotate the rotors within the chambers and it is also easier to manufacture the sample strips, thereby reducing the manufacturing cost.

It is of course to be understood that the invention is not to be restricted to the details of the above embodiments which have been described by way of example only.

For example, the chambers could be arranged so that they are substantially parallel and offset. Any suitable magnetic sensor may be used and so the apparatus is not limited to a Hall Effect sensor. The sample strip could comprise a main body section and a thin lid relative to the body. The heating element could be incorporated into the lid.

In the case of embodiments two or three described above, the primary and the secondary rotors may both have permanent magnetic fields and the electromagnetic field generator could be arranged to drive either the primary or the secondary rotor. The detector may be arranged to detect the rotating magnetic field of the primary or secondary rotors.

The invention claimed is:

1. Apparatus for determining a property of a sample comprising:
    a sample strip including a chamber for receiving at least a part of the sample, a cylindrical rotor that is contained within the chamber, said rotor being arranged to rotate about a longitudinal axis, said rotor having a substantially circular cross-section in a plane substantially perpendicular to and centered about said longitudinal axis, the rotor and the chamber cooperating to define a space therebetween which may be at least partially occupied by the sample, said rotor comprising a permanent magnet which is magnetized across its diameter, said sample strip further including a conduit that leads to the chamber and enables the chamber to be filled with the sample;
    a magnetic drive arranged to drive the rotor; and
    a detector arranged to measure the rate of rotation of the rotor within the chamber.

2. Apparatus as claimed in claim 1, wherein there are two chambers and respective rotors within each chamber.

3. Apparatus as claimed in claim 2, wherein there is a respective detector associated with each chamber.

4. Apparatus as claimed in claim 2, wherein there is a magnetic drive associated with each chamber.

5. Apparatus as claimed in claim 2, wherein the two chambers are substantially adjacent one another, in line with one another or offset relative to one another.

6. Apparatus as claimed in claim 1, wherein the detector is arranged to detect changes brought about by the rotating magnetic field of the rotor.

7. Apparatus as claimed in claim 1, further comprising one or more secondary rotors which are coupled to the rotors in the chambers and the secondary rotors are driven by the or each corresponding magnetic drive thereby indirectly driving the rotors in the respective chambers.

8. Apparatus as claimed in claim 7, wherein the secondary rotors are permanent magnets and the detector detects changes brought about by the rotating magnetic field of the secondary rotors to determine the rate of rotation of the rotors in the respective chambers.

9. Apparatus as claimed in claim 7, wherein the sample strip or the receiving member comprises the secondary rotors.

10. Apparatus as claimed in claim 1, further comprising a heater for heating the sample.

11. Apparatus as claimed in claim 1, further comprising one or more optical detectors for monitoring the presence of the sample in the chamber.

12. Apparatus as claimed in claim 1, further comprising a collection apparatus which is connected to the or each chamber via the conduit, said collection apparatus enabling the sample to be received into the or each chamber.

13. Apparatus as claimed in claim 12, wherein the conduit comprises one or more micro fluidic channels.

14. Apparatus as claimed in claim 1, wherein the chambers and the rotors are substantially cylindrical in shape.

15. Apparatus as claimed in claim 1, wherein the or each detector is a Hall Effect sensor, a magneto-resistive device or a search coil.

16. A sample strip comprising at least one chamber which contains a cylindrical rotor that can rotate within the chamber about a longitudinal axis, said rotor having a substantially circular cross-section in a plane substantially perpendicular to and centered about said longitudinal axis, said rotor comprising a permanent magnet which is magnetized across its diameter, the rotor being adapted to be driven by a magnetic drive, said sample strip further comprising a conduit leading to the chamber to enable the chamber to be at least partially filled with a sample.

17. The sample strip as claimed in claim 16, wherein there are two chambers and respective rotors within each chamber.

18. The sample strip as claimed in claim 16, further comprising one or more secondary rotors which are coupled to the rotors in the chambers and the secondary rotors are driven by the or each corresponding magnetic drive thereby indirectly driving the rotors in the respective chambers.

19. The sample strip as claimed in claim 16, further comprising a collection apparatus which is connected to the or each chamber via the conduit, said collection apparatus enabling the sample to be received into the or each chamber.

20. The sample strip as claimed in claim 16, wherein the chamber and rotor are substantially cylindrical in shape.

21. Apparatus for determining a property of a sample comprising:
a sample strip comprising at least one chamber which contains a cylindrical rotor that can rotate within the chamber about a longitudinal axis, said rotor having a substantially circular cross-section in a plane substantially perpendicular to and centered about said longitudinal axis, said rotor comprising a permanent magnet which is magnetized across its diameter, the rotor being adapted to be driven by a magnetic drive, said sample strip further comprising a conduit leading to the chamber to enable the chamber to be at least partially filled with a sample; and
a receiving member comprising a slot for receiving the sample strip, a magnetic drive adapted to drive the rotor and a detector arranged to detect the rate of rotation of the rotor within the chamber.

* * * * *